United States Patent
Slavitt

[19]

[11] Patent Number: 5,919,193
[45] Date of Patent: Jul. 6, 1999

[54] METHOD AND KIT FOR SURGICALLY CORRECTING MALFORMATIONS IN DIGITS OF A FINGER OR TOE

[76] Inventor: Jerome A. Slavitt, 4023 Log Trail Way, Reisterstown, Md. 21136

[21] Appl. No.: 08/615,829

[22] Filed: Mar. 14, 1996

[51] Int. Cl.$^6$ ....................................................... A61B 17/56
[52] U.S. Cl. .................................. 606/65; 606/72; 606/73; 411/366; 411/923
[58] Field of Search .................................. 606/65, 67, 72, 606/73; 411/191, 192, 366, 378, 379, 387, 411, 923

[56] References Cited

U.S. PATENT DOCUMENTS

| | | | |
|---|---|---|---|
| 2,172,553 | 9/1939 | Tripp | 411/923 |
| 2,242,003 | 5/1941 | Lorenzo | 606/73 |
| 2,382,019 | 8/1945 | Miller | 411/378 |
| 4,116,510 | 9/1978 | Franco | 411/378 |
| 4,581,871 | 4/1986 | Blucher et al. | 411/387 |
| 4,959,064 | 9/1990 | Engelhardt | 606/65 |
| 4,963,144 | 10/1990 | Huene . | |
| 4,969,909 | 11/1990 | Barouk . | |
| 5,098,435 | 3/1992 | Stednitz et al. | 606/73 |
| 5,193,958 | 3/1993 | Day | 411/387 |
| 5,242,447 | 9/1993 | Borzone . | |
| 5,400,805 | 3/1995 | Warren | 606/72 |
| 5,417,692 | 5/1995 | Goble et al. . | |
| 5,425,776 | 6/1995 | Cohen . | |
| 5,511,917 | 4/1996 | Dickson | 411/923 |

*Primary Examiner*—Michael Buiz
*Assistant Examiner*—Daphna Shai
*Attorney, Agent, or Firm*—Bacon & Thomas, PLLC

[57] ABSTRACT

A method to surgically promote the fusion of bone segments together in order to correct bone malformations of the finger or toe involves making an incision in the finger or toe to expose the malformed digit; removing a portion of the malformed digit; forming a bore through each digit from the malformed digit through a tip of the finger or toe; forming a hole, that is aligned with the bore, in a proximal digit; enlarging the diameter of the bore relative to the hole; and inserting a bone screw having a head portion into the bore through the tip of the finger or toe and threadably attaching the bone screw within the hole in the proximal digit until each distal digit is compressed between the head portion of the bone screw and the proximal digit. A tracker member, having a terminal sleeve portion adapted to receive a tip of the bone screw, is provided to guide the screw into the bore through the tip of the finger or toe. Once the screw is fixed in place, the tip of the finger or toe can be stitched with no external objects projecting therefrom. A kit needed to perform the above-described surgical procedure includes various drilling members used to form the bore and hole, the bone screw and the tracker for guiding the bone screw. In addition, a gauge can be provided for measuring the length of the bore in order to select an appropriately dimensioned bone screw.

12 Claims, 5 Drawing Sheets

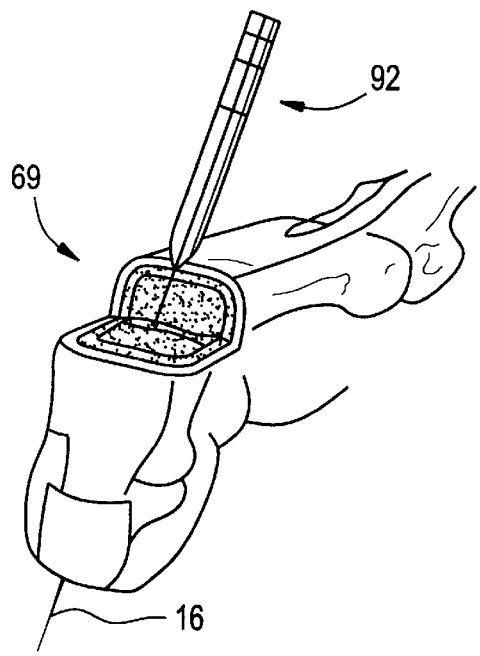
FIG. 15
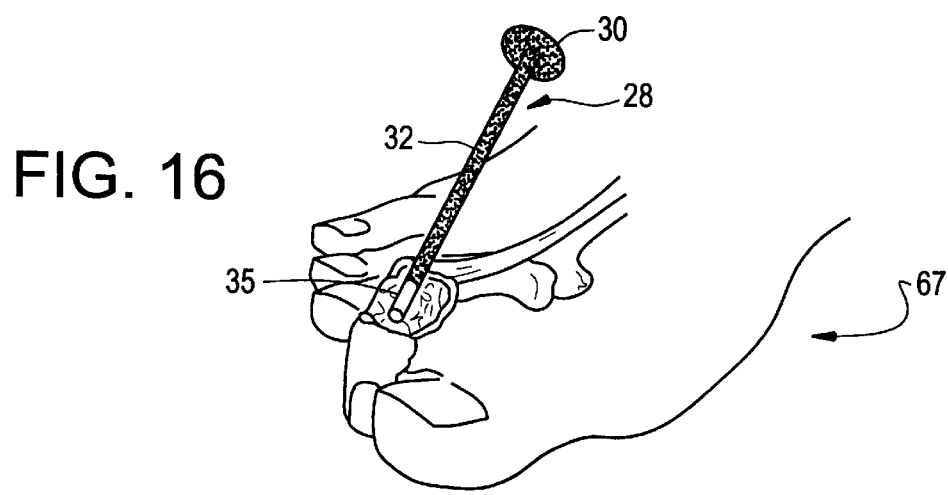
FIG. 16
FIG. 17
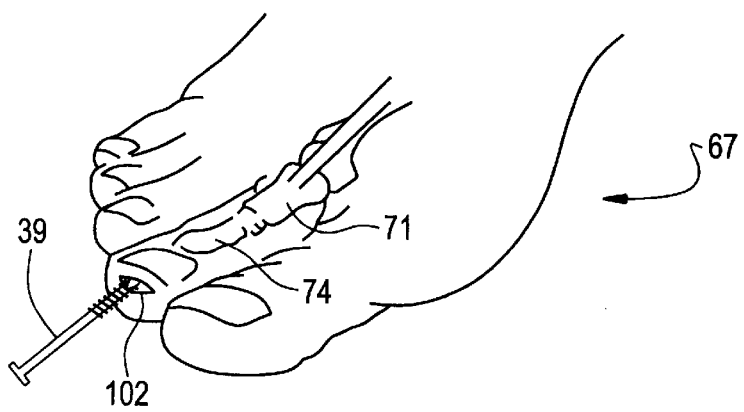

METHOD AND KIT FOR SURGICALLY CORRECTING MALFORMATIONS IN DIGITS OF A FINGER OR TOE

BACKGROUND OF THE INVENTION

1. Field of the Invention

The present invention pertains to the medical art and, more particularly, to the surgical correction of malformations in digits of a finger or toe.

2. Discussion of the Prior Art

Orthopedists and podiatrists have encountered various problems when attempting to fix various types of bones. In particular, the correction of malformations in small bones, such as the digits in fingers and toes, presents significant potential problems. For example, although arthrodesis of the lesser phalanges for the correction of hammertoe deformities, varus rotations, mallet toes and other deformities have been done for many years, over time it has been found that arthroplasty often results in instability of the corrected area. In addition, the affected bone segments have a tendency to deviate over time. Furthermore, this procedure inherently causes a reduction in toe length and provides no joint stability.

The most common surgical method used for correcting or repairing small bones such as in fingers and toes involves the fusing of bone segments together through the use of a K wire. According to such a procedure, the K wire is drilled through the multiple bone segments to be fused together. The K wire remains in place during bone healing and actually protrudes out the end of the finger or toe. Not only does such an arrangement permit a certain degree of relative bone rotation about a longitudinal axis defined by the K wire which is detrimental to the healing process, but the exposed portion of the wire is often snagged on external objects throughout the healing process. In addition, the K wire has to be removed in a second procedure. Exposure of the K wire results in a higher incidence of tract infections.

When addressing common digit malformations such as hammertoe, other types of surgical procedures for correcting or repairing the small bone malformations have been employed, including head resection, peg/hole procedures and implant arthroplasty. Unfortunately, each of these methods also have their associated drawbacks For example, although head resection techniques can be quick and easy, they can result in medial/lateral bone hypertrophy, excessive toe shortening and flail toe. Peg/hole techniques require greater surgical skill as compared to K wire procedures, have associated therewith increased surgical times and utilize cumbersome external fixative devices. Finally, implant arthroplasty requires even greater surgical technique as it involves the implantation of foreign matter into the patient's body, which foreign matter may be rejected by the patient's body. Edema is also associated with such procedures and the implant actually only serves as a spacer for the digits.

Therefore there exists a need in the art for improved surgical devices and procedures for correcting or repairing malformations in the digits of a finger or toe which at least obviates the need for advanced surgical skills, minimizes the potential for infections and reduces the degree of shortening of the finger or toe, while also improving the union of bones.

SUMMARY OF THE INVENTION

The invention is directed to a unique method to surgically promote the fusion of bone segments together in order to correct bone malformations of the finger or toe, as well as a kit needed to perform the method. More specifically, the method involves making an incision in the finger or toe to expose the malformed digit; removing a portion of the malformed digit; forming a bore through each digit from the malformed digit through a tip of the finger or toe; forming a hole, that is aligned with the bore, in a proximal digit; enlarging the diameter of the bore relative to the hole; and inserting a bone screw having a head portion into the bore through the tip of the finger or toe and threadably attaching the bone screw within the hole in the proximal digit until each distal digit is compressed between the head portion of the bone screw and the proximal digit. A tracker member, having a terminal sleeve portion adapted to receive a tip of the bone screw, is provided to guide the screw into the bore through the tip of the finger or toe. Once the screw is fixed in place, the tip of the finger or toe can be stitched with no external objects projecting therefrom.

The kit needed to perform the above-described surgical procedure includes various drilling members used to form the bore and hole, the bone screw and the tracker for guiding the bone screw. In addition, a gauge can be provided for measuring the length of the bore in order to select an appropriately dimensioned bone screw.

In accordance with the invention, the bone segments or digits are placed under compression while the bone-to-bone contact area is increased in order to enhance the fusion process and provide a more rigid bone fixation. By screwing the small digits together with a bone screw that is fully located under the skin, the possibility of infection is minimized since no attachment elements are exposed. The bone screw is formed from a bio-safe material so it can remain in the patient or can be later surgically removed.

Additional features and advantages of the invention will become more readily apparent from the following detailed description of a preferred embodiment thereof when taken in conjunction with the drawings wherein like references numerals refer to corresponding parts in the several views.

BRIEF DESCRIPTION OF THE DRAWINGS

FIG. 15 is a view similar to FIG. 14 at a sixth operational stage of the invention;

FIG. 16 is a view similar to FIG. 15 at a seventh operational stage of the invention;

FIG. 17 is a view similar to FIG. 16 at a eighth operational stage of the invention.

DETAILED DESCRIPTION OF THE PREFERRED EMBODIMENT

Figure 1:
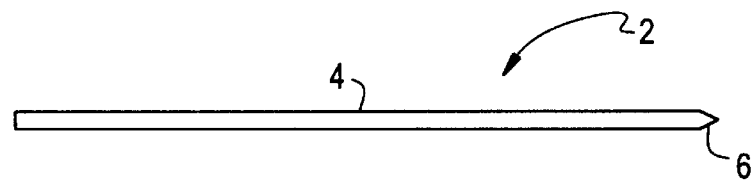
FIG. 1 is a plan view of a first drill bit member utilized in accordance with the invention.
Figure 2:
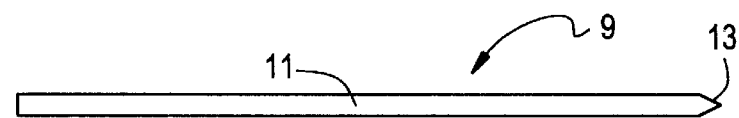
FIG. 2 is a plan view of a second drill bit member according to the invention.
Figure 3:
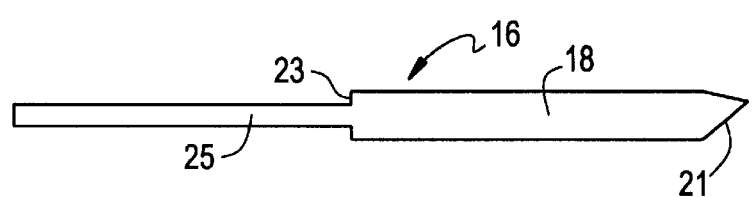
FIG. 3 is a plan view of a third drill bit member.

The various elements incorporated in the kit and used in the surgical method of the invention will first be described with successive references to FIGS. 1–8. FIG. 1 shows a first drill bit member 2 having a cylindrical shaft 4 that terminates in a point 6 at one end thereof FIG. 2 shows a second drill bit member 9 that is defined by a shaft 11 having a pointed end 13. Basically, the only difference between first and second drill bit members 2 and 9 is the respective diameters of shafts 4 and 11. In the preferred embodiment, both first and second drill bit members 2 and 9 are defined by K wires having diameters of 0.045 and 0.062 inches (approx. 1.1 and 1.6 mm) respectively. FIG. 3 illustrates a third drill bit member 16 including a first shaft portion 18 having a first, pointed end 21 and a second end 23 that leads to a reduced diameter shaft portion 25. In the preferred embodiment, first shaft portion 18 has as associated diameter of 0.072 inches (1.8 mm) and reduced diameter shaft portion 25 has a diameter of 0.062 inches (1.6 mm). Of course, these diameters are only given for exemplary purposes and can vary in accordance with the invention, generally depending on the size of the bones being surgically repaired.

Figure 4:
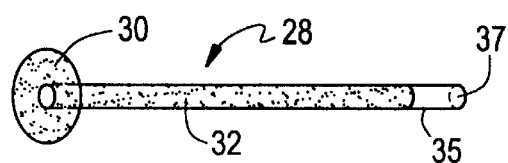
FIG. 4 is a perspective view of a tracker incorporated in the invention.
Figure 7:
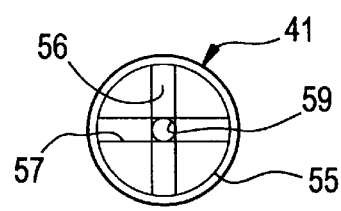
FIG. 7 is a top view of the bone screw of FIG. 5.
Figure 5:
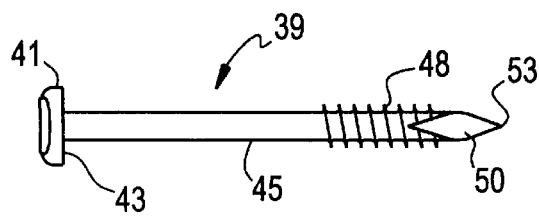
FIG. 5 is a side view of a bone screw used in the invention.
Figure 8:
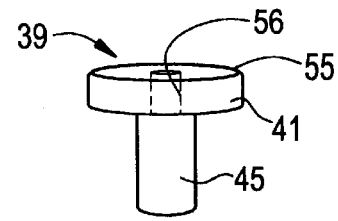
FIG. 8 is a partial perspective view of a top end portion of the bone screw of FIG. 5.
Figure 6:
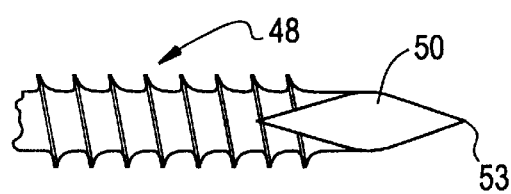
FIG. 6 is an enlarged side view of an end portion of the bone screw of FIG. 5.

FIG. 4 illustrates a preferred embodiment of a tracker 28 incorporated in the invention. Tracker 28 is preferably formed from stainless steel and functions as a guiding member as will be discussed in detail hereinafter and includes a manual grasping knob 30 from which extends an elongate rod 32. Rod 32 terminates in a sleeve portion 35. An opening 37 leads into terminal sleeve portion 35. In accordance with the invention, only sleeve portion 37 needs to be hollow and therefore elongate rod 32 may be solid or tubular without departing from the invention. Given the examplary diameters for drill bit members 2, 9 and 16 above, rod 32 would have a maximum outer diameter of 0.072 inches (1.8 mm) and opening 37 has an associated diameter in the range of 0.045 inches (1.1 mm).

Reference is now made to FIGS. 5–8 in describing the preferred construction of the bone screw 39 according to the invention. Bone screw 39 has a head portion 41 that ends in a flat side 43. Extending from flat side 43 is a shank portion 45 which leads to a threaded portion 48 preferably defined by a single, spiraling thread. As shown, threaded portion 48 constitutes an enlarged diametric portion of bone screw 39 and is formed with a shaved section 50 such that screw 39 is self-tapping and terminates in an extended tapered point 53. Head portion 41 is rounded at 55 and is formed with criss-crossing grooves 57 and a central recessed hole 59 that is adapted to receive a screwdriver (not shown) commonly used in the medical art. The surgical elements described above are preferably provided as a kit for use with conventional medical instruments such as a scalpel, a fine oscillating saw, a drill and a screwdriver to surgically correct a digit malformation in a finger or toe. The use of these elements in an exemplary surgical operation will now be described with reference to FIGS. 9–18 which illustrate the surgical repair of a hammertoe.

Figure 9:
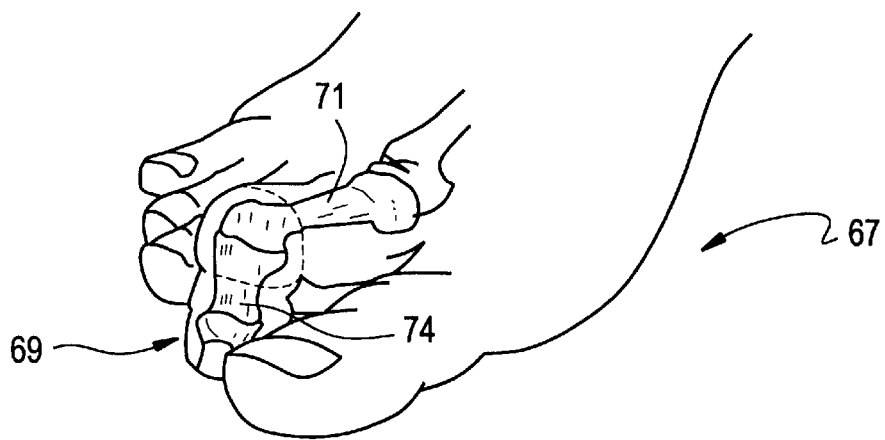
FIG. 9 is a perspective view of foot having a hammertoe.
Figure 10:
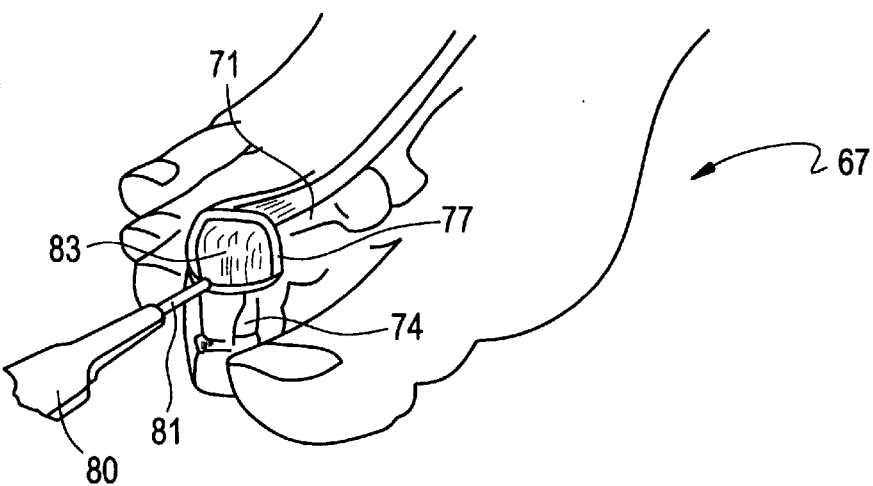
FIG. 10 is a view similar to FIG. 9 but after an initial incision is made in accordance with the invention.
Figure 11:
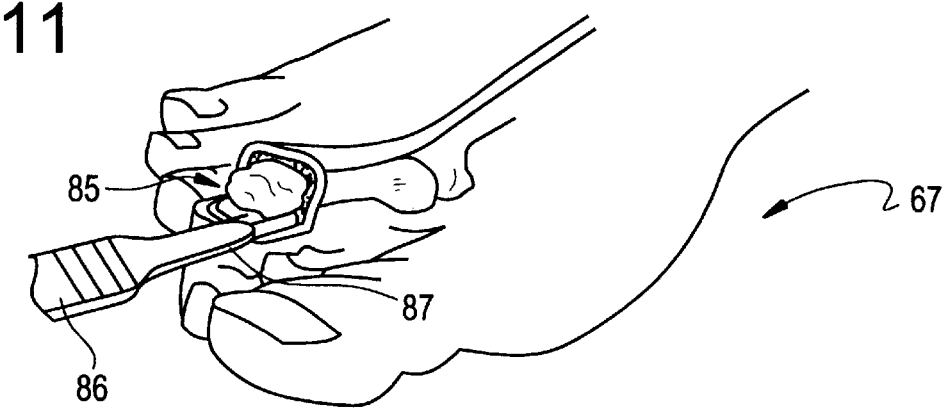
FIG. 11 is a view similar to FIG. 10 at a second operational stage of the invention.

FIG. 9 illustrates a portion of a human foot 67 in which the second toe 69 has a malformation commonly known as hammertoe. As shown, the malformation is between the proximal phalanx or digit 71 and the intermediate phalanx or digit 74. Initially, an incision 77 is made as shown in FIG. 10 by means of a scalpel 80 having a blade 81. Incision 77 can take any form conventionally known and therefore can be linear, semi-elliptical, "H", etc. type incisions. Once incision 77 is accomplished, deeper dissection is performed with resection of tendon 83 and sub-Q if needed to fully expose malformation 85. A second scalpel 86 can be utilized to sever the collateral ligaments 87 as best shown in FIG. 11 or the ligaments may be repositioned by other surgical instruments.

Figure 12:
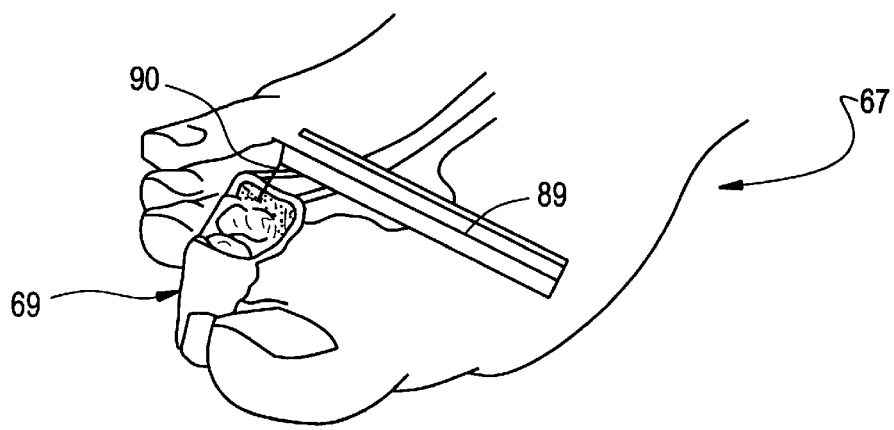
FIG. 12 is a view similar to FIG. 11 at a third operational stage of the invention.
Figure 13:
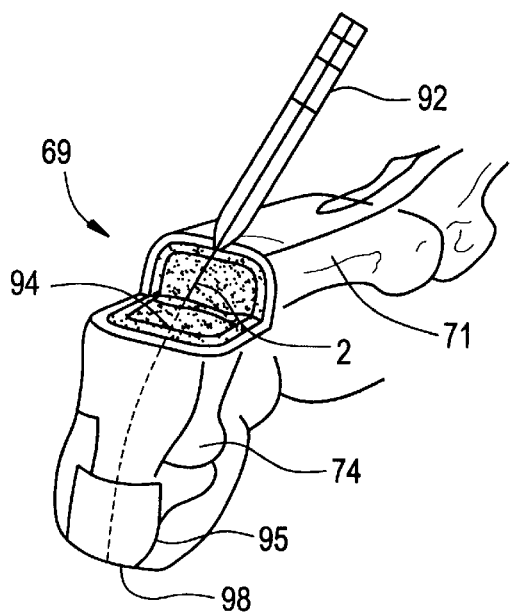
FIG. 13 is a view similar to FIG. 12 at a fourth operational stage of the invention.

In the next step, as shown in FIG. 12, a fine oscillating saw 89 having a blade 90 removes the articulation surfaces at malformation 85. This removal of the articulation surfaces at malformation 85 can be performed with blade 90 either ninety degrees to the shaft or angled to correct rotation as necessary. In general, all of the steps so far described are conventional. After the articulation surfaces at malformation 85 are removed, a drill 92 having first drill bit member 2 mounted therein is used to form a longitudinal bore 94 through intermediate digit 74, a distal digit 95 and out a remote end 98 of toe 69 as illustrated in FIG. 13. Intermediate digit 74 is then realigned with proximal digit 71 (not shown in the drawings) and first drill bit member 2 is retrograded back through remote end 98 of toe 69, distal digit 95 and intermediate digit 74 in order to form a hole 100 (see FIG. 14) in proximal digit 71. Hole 100 is adapted to receive extended tapered point 53 of screw 39 and functions to guide the initial screwing of screw 39 into proximal digit 71 as will be discussed more fully below.

Figure 14:
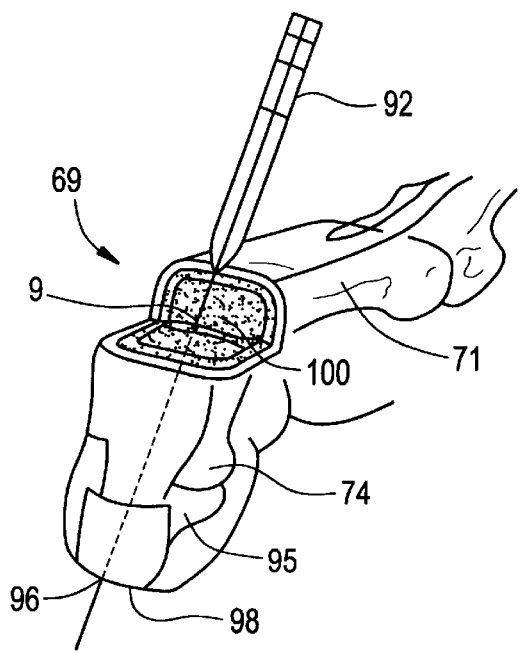
FIG. 14 is a view similar to FIG. 13 at a fifth operational stage of the invention.

Thereafter, longitudinal bore 94 in intermediate digit 74 and distal digit 95 is overdrilled with second drill bit member 9 as shown in FIG. 14 and further by third drill bit member 16 as illustrated in FIG. 15. At this point, all drilling stages are complete and a depth gauge, which is not illustrated but which basically constitutes a K wire that has indicia provided along its length, can be inserted to determine the length of longitudinal bore 94 in order to select an appropriate length screw 39. As shown in FIG. 16, tracker 28 is positioned within longitudinal bore 94 and extends out an access opening 102 (also see FIG. 17) formed in remote end 98 of toe 69. As shown, access opening 102 has been enlarged by an incision in order to readily accommodate head portion 41 of screw 39. Tracker 28 is preferably provided since it has been found to sometimes be cumbersome to readily access longitudinal bore 94 through opening 102. With tracker 28 extending through longitudinal bore 94 and out access opening 102, extended tapered point 53 of screw 39 can be inserted within terminal sleeve portion 35 of tracker 28 and then tracker 28 and screw 39 can be simultaneously shifted to guide screw 39 into longitudinal bore 94. At this point it should be realized that screw 39 has an outermost diameter at threaded portion 48 (not including the diameter of head portion 41) so that screw 39 readily slides through longitudinal bore 94. Once the proximal, intermediate and distal digits 71, 74 and 95 are aligned, extended tapered point 53 can be positioned within hole 100 in the proximal digit 71 and a screwdriver can be applied against head portion 41 at criss-crossing grooves 56 and 57, as well as central recessed hole 59, to threadably attach screw into proximal digit 71. This threading operation will continue until head portion 41 of screw 39 abuts distal digit 95 whereupon intermediate digit 74 will be compressed against proximal digit 71. Access opening 102 can then be closed over the head portion 41 of screw 39 such as through conventional stitching. Toe 69 is allowed to heal in this position with the screw completely within the repaired toe.

Figure 18:
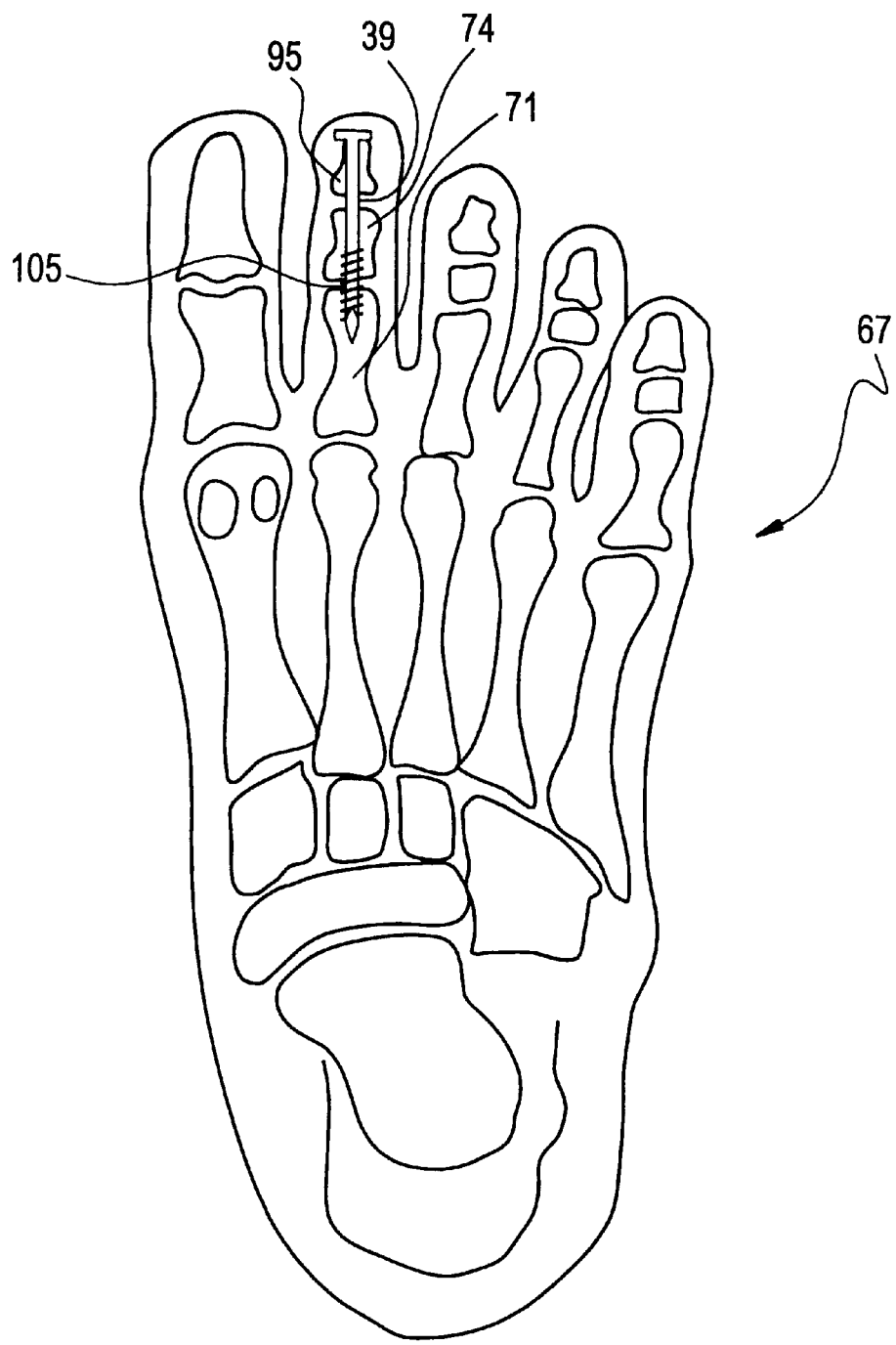
FIG. 18 is a cut-away view of a foot following a surgical operation in accordance with the invention.

FIG. 18 illustrates the correction of the hammertoe malformation in toe 69 of foot 67. As shown in this figure, intermediate digit 74 becomes joined with proximal digit 71 through a fusion zone 105 following a suitable healing period. In the preferred embodiment, screw 39 is made of stainless steel or other known biocompatible material and therefore can remain within foot 67. If desired, screw 39 can be removed following complete fusion of the bones. In any event, since screw 39 is positioned completely within foot 67 following the operation and access opening 102 is closed, there is no external element maintained outside the toe during the healing process which can be undesirably caught on objects or which can be the source of future infection.

Although described with respect to a preferred embodiment of the invention, and with reference to a particular type of malformation, it should be readily understood that various changes and/or modifications made be made to the invention without departing from the spirit thereof For example, although the shank portion of bone screw is described as being of a smaller diameter than the threaded portion of the bone screw, it is only important that the shank portion readily slide within the formed longitudinal bone and therefor could have a diameter that is equal to that of the threaded portion. In fact, the shank portion could also be threaded so long as the outer diameter of the threads is less than the diameter of the longitudinal bore. In general, the invention is only intended to be limited by the scope of the following claims.

I claim:

1. A method of surgically correcting malformations in digits of a finger or toe comprising:

making an incision in a finger or toe to expose a malformed digit;

removing at least a portion of the malformed digit;

forming a longitudinal bore that extends from the incision, through each distal digit between the malformed digit and a remote end of the finger or toe, and out of the remote end of the finger or toe so as to define an access opening with a first drill member having a first diameter;

aligning each distal digit through which the longitudinal bore extends with a proximal digit located on an opposing side of the incision;

utilizing the longitudinal bore as a guide when inserting a drilling member therein from the remote end of the finger or toe back past the incision and then drilling a hole into the proximal digit;

re-drilling the longitudinal bore formed in each distal digit with a second drilling member having a second diameter which is greater than said first diameter;

inserting through said access opening and said longitudinal bore a one-piece bone screw for use in the correction of malformations in digits of a finger or toe comprising a flat, non-threaded head portion, a shank portion extending longitudinally from said head portion, said shank portion being cylindrical in shape, and a threaded portion extending longitudinally from said shank portion away from said flat, non-threaded head portion, said threaded portion comprising a continuous spiraling thread, terminating in a extended tapered point, wherein said bone screw is sized to be inserted in a longitudinal bore formed in at least one digit distal to a malformation in a finger or toe and threadably attached to a digit proximal to the malformation in order to interconnect the distal and proximal digits by compressing the at least one distal digit between the head portion of the bone screw and the proximal digit; and threadably securing said threaded portion within the hole formed in said proximal digit until each said distal digit is compressed between the head portion of said bore screw and the proximal digit to provide permanent relative positioning of the distal and proximal digits.

2. The method according to claim 1, further comprising:

providing a trocar point at an end of the threaded portion of the bone screw remote from the head portion; and inserting the trocar point into the hole of the proximal digit prior to threadably securing the bone screw in order to further guide the bone screw and reduce relative lateral movement between the distal and proximal digits as the bone screw is tightened.

3. The method according to claim 1, further comprising, prior to inserting the bone screw through said access opening:

inserting a guide tracker having a terminal sleeve portion through the longitudinal bore and out the access opening;

placing a tip of said bone screw in the terminal sleeve portion; and guiding the tip of said bone screw through said access opening and into said longitudinal bore with said guide tracker.

4. The method according to claim 1, further comprising enlarging the access opening to readily permit the head portion of said bone screw to pass therethrough.

5. The method according to claim 1, further comprising, prior to inserting the bone screw through said access opening, measuring a depth of said longitudinal bore and selecting the bone screw based on the measured depth.

6. A surgical kit for use in the correction of malformations in digits of a finger or toe comprising:

a first drill bit member having a first diameter;

a second drill bit member having a second diameter which is greater than said first diameter;

a tracker having an elongated shaft and a terminal sleeve portion; and a one-piece bone screw for use in the correction of malformations in digits of a finger or toe comprising a flat, non-threaded head portion, a shank portion extending longitudinally from said head portion, said shank portion being cylindrical in shape, and a threaded portion extending longitudinally from said shank portion away from said flat, non-threaded head portion, said threaded portion comprising a continuous spiraling thread, terminating in a extended tapered point, wherein said bone screw is sized to be inserted in a longitudinal bore formed in at least one digit distal to a malformation in a finer or toe and threadably attached to a digit proximal to the malformation in order to interconnect the distal and proximal digits by compressing the at least one distal digit between the head portion of the bone screw and the proximal digit.

7. The surgical kit according to claim 6, further comprising a gauge for measuring the depth of the longitudinal bore in order to select said bone screw.

8. The surgical kit according to claim 6, wherein the shank portion of said bone screw has a smooth outer peripheral surface.

9. A one-piece bone screw for use in the correction of malformations in digits of a finger or toe comprising:
   a flat, non-threaded head portion;
   a shank portion extending longitudinally from said head portion, said shank portion being cylindrical in shape; and
   a threaded portion extending longitudinally from said shank portion away from said flat, non-threaded head portion, said threaded portion comprising a continuous spiraling thread, terminating in a extended tapered point, wherein said bone screw is sized to be inserted in a longitudinal bore formed in at least one digit distal to a malformation in a finger or toe and threadably attached to a digit proximal to the malformation in order to interconnect the distal and proximal digits by compressing the at least one distal digit between the head portion of the bone screw and the proximal digit.

10. The bone screw according to claim 9, wherein said shank portion has an outer diameter that is less than an outer diameter of said threaded portion.

11. The bone screw according to claim 9, wherein said shank portion has a generally smooth outer surface.

12. The bone screw according to claim 9, wherein said shank portion is threaded.

* * * * *